United States Patent [19]
Dury

[11] Patent Number: 5,245,411
[45] Date of Patent: Sep. 14, 1993

[54] OPTICAL INSTRUMENT AND CONVEYOR FOR AUTOMATED OPTICAL INSPECTION MACHINE AND METHODS OF OPERATION

[75] Inventor: K. Kyle Dury, Yardley, Pa.

[73] Assignee: Stark Yttrium, Yardley, Pa.

[21] Appl. No.: 753,935

[22] Filed: Sep. 3, 1991

[51] Int. Cl.$^5$ ............................................. G01N 21/47
[52] U.S. Cl. ..................................... 356/446; 356/445;
356/237; 356/73; 356/376; 356/384; 209/586
[58] Field of Search ........................... 356/445–446,
356/73, 237, 238, 328, 376, 240, 383, 384;
209/586

[56] References Cited

U.S. PATENT DOCUMENTS 4,776,022 10/1988 Fox et al. .............................. 356/237
4,919,535  4/1990 Hohberg et al. ...................... 356/446

Primary Examiner—Vincent P. McGraw
Assistant Examiner—LaCharles Keesee
Attorney, Agent, or Firm—Nixon & Vanderhye

[57] ABSTRACT

The optical instrument includes a body mounted for X-Y movement above a generally planar object and carries a wide-angle lens, and a plurality of collecting mirrors disposed at angular locations about and spaced from the axis of the lens. A reversing mirror is located above the lens and sensors are disposed in the instrument. The images from the surface under observation are reflected by the collecting mirrors through the wide-angle lens against the reversing mirror for imaging on the sensors. The light is transposed into electrical signals for analysis in a computer. The conveyor for conveying the generally planar object clamps the lateral margins of the object and includes sections movable generally in the direction of the axis of the lens and independently of one another to ensure that the surface of the object under observation lies in a plane generally parallel to a horizontal plane.

13 Claims, 8 Drawing Sheets

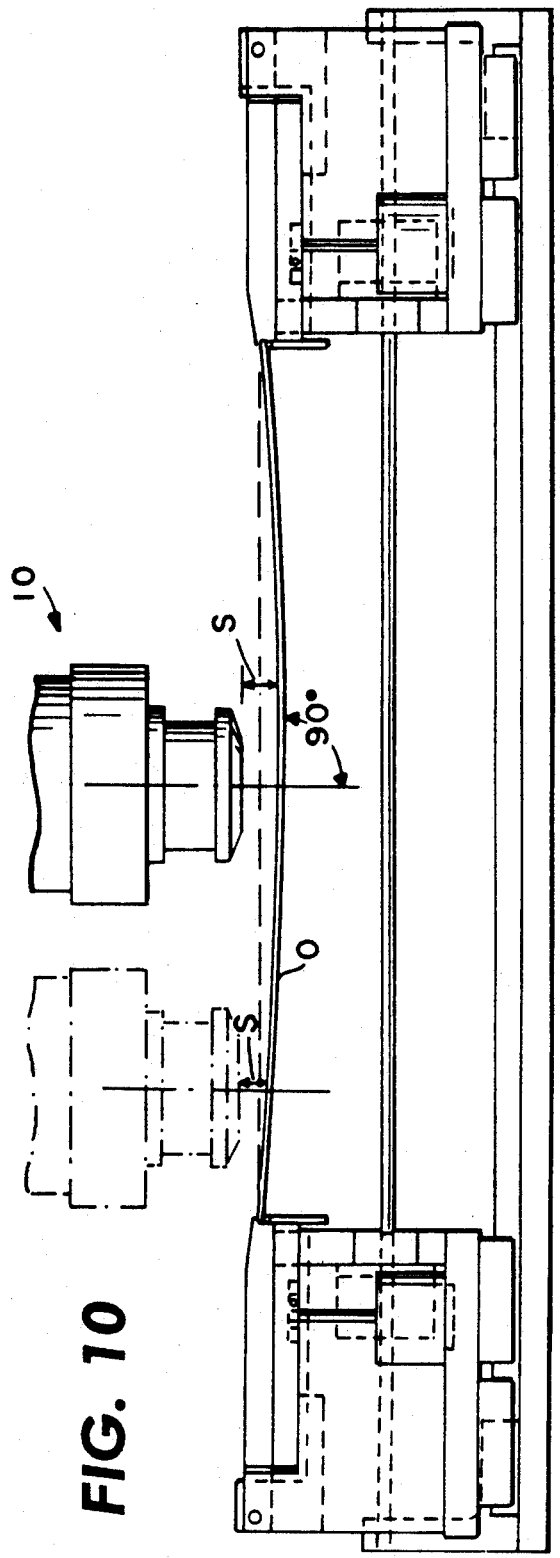
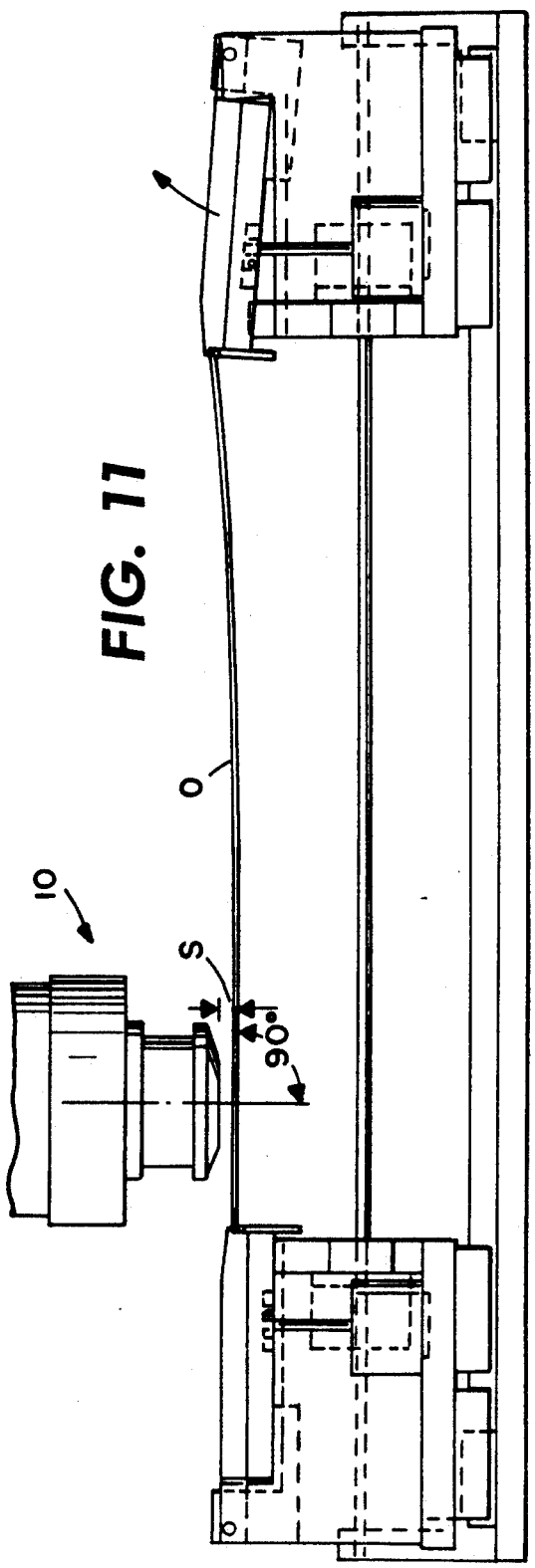

OPTICAL INSTRUMENT AND CONVEYOR FOR AUTOMATED OPTICAL INSPECTION MACHINE AND METHODS OF OPERATION

BACKGROUND AND SUMMARY OF THE INVENTION

The present invention relates to an optical instrument and a conveyor associated to provide undistorted, sharply focussed images simultaneously from different angular locations about an object being conveyed, and particularly relates to an inspection machine for visually inspecting the assembly of the components of a circuit board during manufacturing.

In various manufacturing processes, it is frequently necessary and desirable to automatically optically inspect manufactured components for accuracy in their location and structure. For example, in the manufacture of circuit boards, it is customary to optically inspect the three-dimensional structure of the components of the circuit boards as they pass through the manufacturing process. It will be appreciated that circuit boards are generally planar but that the leads of the circuit board components and connecting.(solder) surfaces are generally very small and fully three-dimensional. Thus, circuit boards are conventionally conveyed through an inspection station for this purpose and typically by a conveyor which grasps the opposite side margins of the board to convey the board. It has been difficult, however, to accurately assess the correct assembly of very small, for example, 5 to 10 mm components, with existing optical equipment. A principal cause of this difficulty is in the inability of such existing equipment to eliminate perspective distortion of the optical image and obtain uniform imaging of an angled surface of the object. Moreover, it has been difficult to obtain undistorted perspective images of the object from different angular locations about the object with uniform focus, brightness and magnification and particularly in a light, rigid and compact optical inspection head capable of inspecting all areas of the circuit board It will be appreciated that circuit boards may range in size from 1×1 to about 20×20 square inches. These difficulties are further compounded by the distortion in the image caused by the weight of the board and its components when the board bows or sags between its oppositely supported marginal edges It will be appreciated that all portions of the board do not therefore present a surface at all times in a horizontal plane correctly spaced relative to the lens of an optical instrument located close to the board to inspect these portions of the board. Efforts to compensate for this sag or bow or, more generally, the lack of coplanarity of the observed portion of the board and a plane normal to the axis of the lens of the optical instrument have resulted in the necessity for complicated computer processing of the resultant images.

In accordance with the present invention, there is provided an optical instrument, e.g., a vision head and a conveyor, which comprise an optical inspection machine for inspecting small objects, or small portions of larger objects, on the conveyor in a manner in which undistorted perspective images of the portions of the object from different angular locations about the object are simultaneously obtained for analysis and comparison with predetermined information regarding the structure of that portion of the object. To accomplish this, there is provided a vision head mounted on a carriage for traversing movement in a plane, for example, in an X-Y plane, relative to a generally parallel plane in which the object under observation is conveyed. The vision head includes a wide angle lens, a plurality of collecting mirrors, a reversing mirror, illumination sources for illuminating the object and sensors for transposing the light signals of the images into electrical signals which may be digitized for general analysis and comparison with predetermined information regarding that structure of the object.

More particularly, the vision head includes a wide angle lens, the axis of which passes normal to the plane of conveyance of the object under observation. Radially disposed about and spaced from the axis and between the lens and the object are a plurality of collecting mirrors. In a preferred embodiment, light-emitting diodes are arranged below the collecting mirrors for illuminating the object. Accordingly, light rays representing the image of the object from different angular locations about the wide angle lens axis are reflected from the collecting mirrors through the wide angle lens. A reversing mirror receives the light rays from the wide angle lens and reflects those rays onto sensors for conversion into electrical signals for later digitization and analysis Thus, the vision head creates a plurality of crisp images of a single three-dimensional region under observation where each image view is at a large angle to the lens axis, e.g., 25° to 45°, and at different angular locations about the lens axis, e.g., 0° to 360°. Moreover, each image is uniformly focussed without perspective distortion and with uniform brightness and uniform magnification. Hence, all three-dimensional surfaces of the object are clearly in focus and undistorted. Moreover, the vision head or carriage may be fabricated as a single machined part, with only 0° and 90° machining operations thereby enabling inexpensive precision fabrication of the vision heads. The optical arrangement is also compact and light, allowing rapid movement of the vision head relative to the object under observation and in a very small space.

More particularly, circuit boards, when conveyed along a plane of conveyance, will normally sag or bow along the middle. The sag or bow oftentimes exceeds the depth of focus of automated optical inspection equipment, particularly when viewed at an angle from the vertical, as is necessary for surface measurements and for solder shape examination. Additionally, this sag or bow may displace images to the extent that particular points of the portion of interest are not contained in the image. To compensate for the the irregular spacing and lack of planarity between the object under observation and a plane normal to the axis of the lens, i.e., to compensate for a bow or sag in the circuit board whereby an angle is extant between the plane of conveyance and the surface of the board at the area of observation, a conveyor according to the present invention provides for relative movement of the conveyor sections supporting the margins of the object generally in a direction parallel to the axis of the lens. Where the object sags or bows between the margins, it will be appreciated that, by displacing one of the margins of the object under observation relative to the other margin, the small discrete area under observation may obtain a position substantially parallel to a plane normal to the axis of the lens. By clamping the board at the margins and displacing one margin relative to the other margin in a direction parallel to the axis of the lens, the level or tilt of the circuit board surface at each observable location between the margins may be adjusted into coplanar relation with a plane normal to the axis of the lens.

An additional benefit is that the object can be moved vertically so all images are of the same region of the object, which increases inspection speed.

More particularly, each side section of the conveyor is provided with upper and lower clamping plates. An endless-loop conveyor belt is disposed between the clamping plates The clamping plates are pivoted about a common horizontal axis generally parallel to the direction of conveyance. When a circuit board is introduced into the conveyor, the belt advances the board between the clamping plates. The board is then held fixed, preferably horizontally, between each conveyor section, while the vision head moves in an X-Y plane about and above the board for observing predetermined portions of the board. Each side section may be adjusted independently relative to the other side section to adjust the tilt and level of the surface of the board then under observation by the vision head. Particularly, linear actuators pivot the clamping elements about the pivot axis to effect the relative displacement of the side conveyor sections relative to one another. Additionally, horizontal linear actuators may be used to adjust the width of the conveyor sections relative to one another to accommodate different widths of circuit boards.

In a preferred embodiment according to the present invention, there is provided an optical device for providing discrete, undistorted and uniform images of an object or a small region of an object lying in a plane and having three-dimensional surfaces, with each image taken at a different angular location about an axis passing perpendicularly through the plane and object, comprising a wide angle lens spaced from the object and disposed along the axis, a plurality of collecting mirrors spaced from and disposed at predetermined angular locations about the axis, the mirrors lying in planes generally parallel to the axis and for disposition between the wide angle lens and the object for reflecting light rays from the object through the wide angle lens and means for receiving the light rays passing through the wide angle lens from the object and the collecting mirrors representing an undistorted image of the object as viewed from each angular location with uniform focus of the three dimensional surfaces of the object.

In a further preferred embodiment according to the present invention, there is provided a conveyor for conveying an object having surface portions in a first plane and displacing such surface portions into a second, different plane, comprising first and second conveying sections spaced one from the other with each section including means for engaging marginal portions of an object spanning between the sections for conveying the object in a predetermined direction of conveyance and means carried by each of the first and second conveyor sections for displacing the respective margins of the object in a direction generally normal to the direction of conveyance and independently of one another whereby a specified portion of the object in the first plane may be disposed in the second plane.

In a further preferred embodiment according to the present invention, there is provided a visual inspection machine for visually inspecting surface portions of generally planar objects comprising a conveyor for conveying the planar objects with each planar object having general surface portions in a first plane and displacing such surface portions into a second, different plane, the conveyor including first and second conveying sections spaced one from the other with each section including means for engaging a marginal portion of the planar object spanning between the sections for conveying the element in a predetermined direction of conveyance, means carried by each of the first and second conveyor sections for displacing the respective margins of the element in a direction generally normal to the direction of conveyance and independently of one another whereby a specified surface portion of the planar object in the first plane may be disposed in the second plane. Also provided is an optical device for providing discrete undistorted images of the surface portion of the object when lying in the second plane and disposed in spaced registration with an object on the conveyor, a wide angle lens spaced from the surface portion of the object and having an axis generally normal to the second plane and a plurality of collecting mirrors spaced from and disposed at predetermined angular locations about the axis, the mirrors lying in planes generally parallel to the axis and for disposition between the wide angle lens and the object for reflecting light rays from the object through the wide angle lens and means for receiving the light rays passing through the wide angle lens from the object and the collecting mirrors representing an undistorted image of the object as viewed from each angular location with uniform focus of the three dimensional surfaces of the object.

In a further preferred embodiment according to the present invention, there is provided a method of optically inspecting an object, comprising the steps of conveying an object in a first predetermined direction with a surface portion of the object in a first plane, displacing a margin of the object in a direction generally normal to the direction of conveyance and independently relative to an opposite margin of the object to reorient the surface portion from the first plane into a second plane different from the first plane, providing a wide angle lens having an axis generally normal to the surface portion in the second plane and a plurality of collecting mirrors about the axis and between the lens and the surface portion and optically forming images of the surface portion of the object in the second plane from different angular locations about the axis with each image representing an undistorted image of the surface portion as viewed from each angular location with uniform focus of the three-dimensional surfaces of the object.

Accordingly, it is a primary object of the present invention to provide a novel and improved optical instrument, e.g., a vision head for visual inspection of predetermined areas of an object whereby undistorted perspective images of the object at different angular locations about the object are afforded.

It is another object of the present invention to provide a novel and improved conveyor for conveying an object for visual inspection wherein the predetermined areas of observation of the object may be tilted and levelled as needed for accurate observation by displacement of the side sections of the conveyor carrying the margins of the object relative to and independently of one another.

It is a still further object of the present invention to provide a novel and improved visual inspection machine affording undistorted perspective images of objects under observation at different angles about the objects for comparison with predetermined information whereby irregularities in the observed surface can be ascertained.

These and further objects and advantages of the present invention will become more apparent upon reference to the following specification, appended claims and drawings.

BRIEF DESCRIPTION OF THE DRAWING FIGURES

Figure 3:
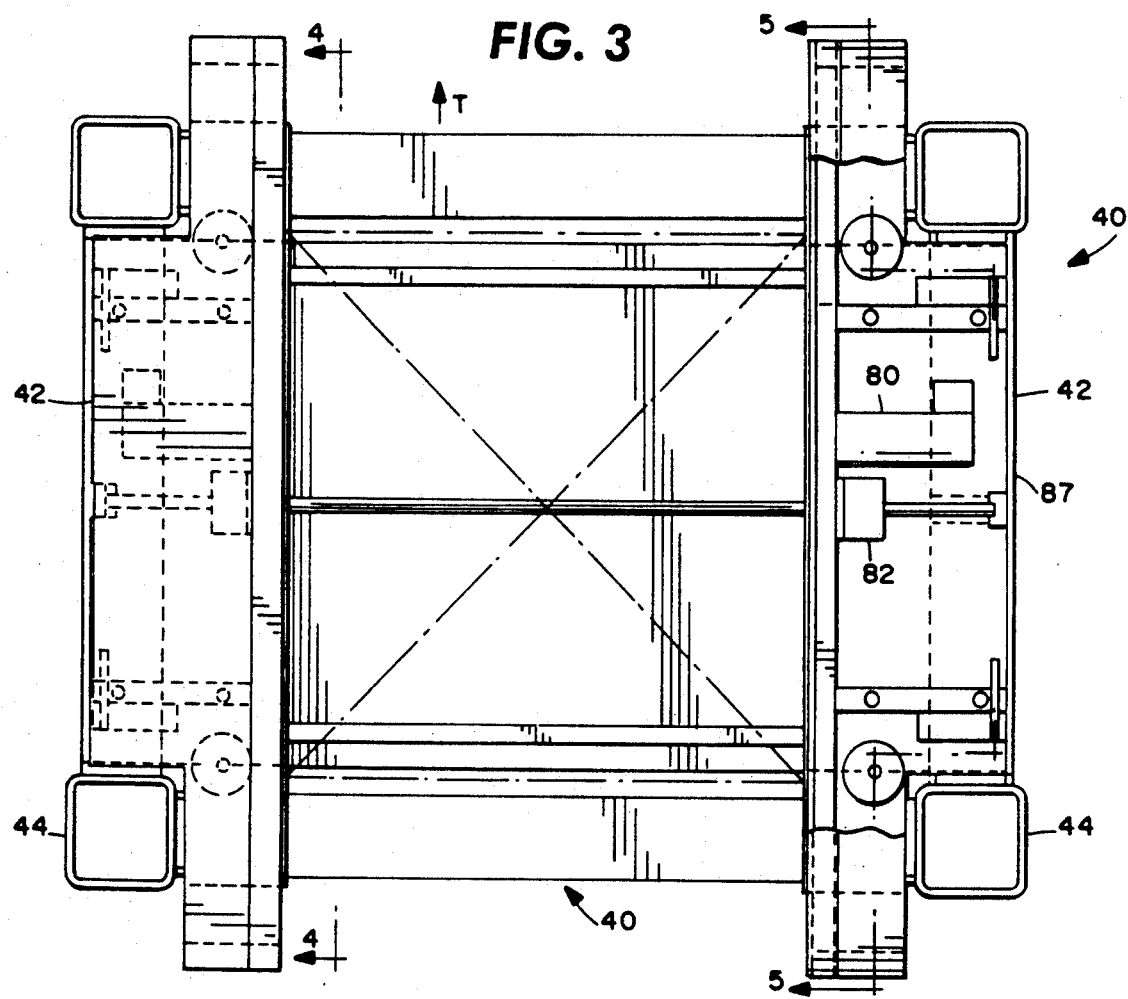
FIG. 3 is a plan view, with parts broken out for illustrative purposes, of a conveyor constructed in accordance with the present invention.
Figure 4:
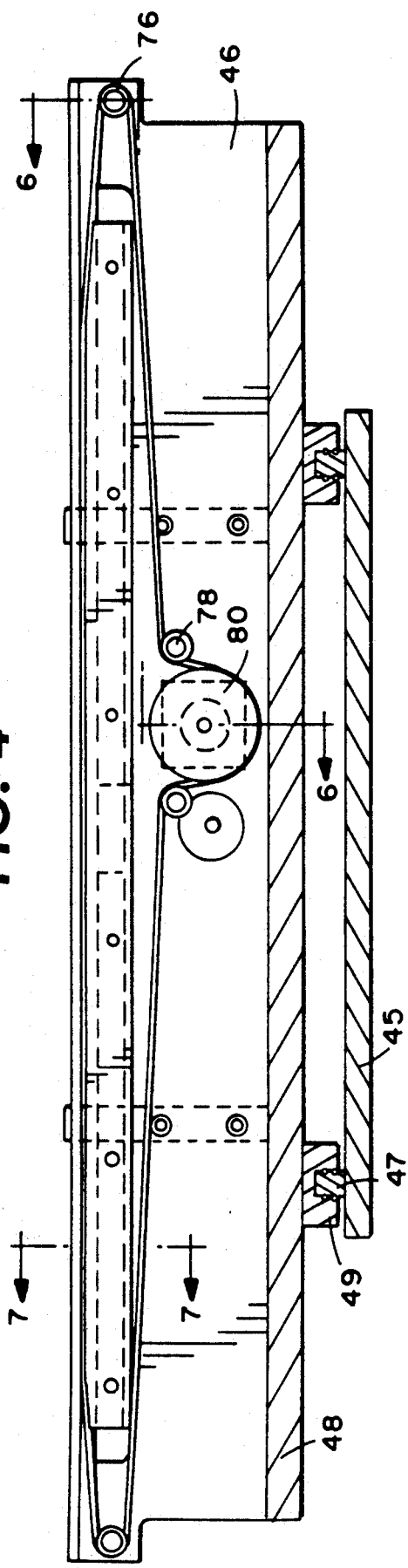
Figure 5:
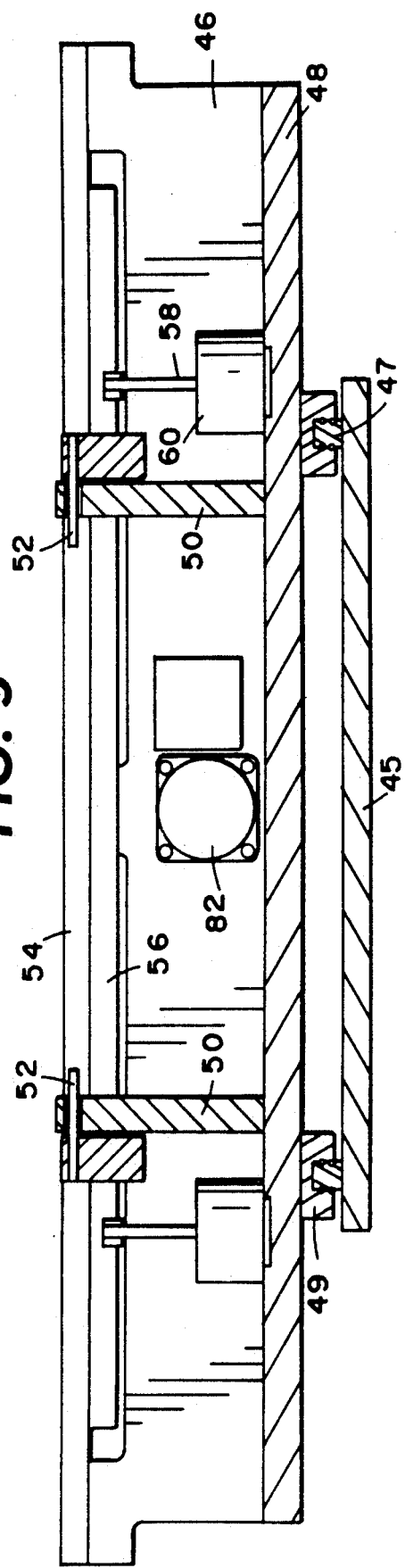
Figure 7:
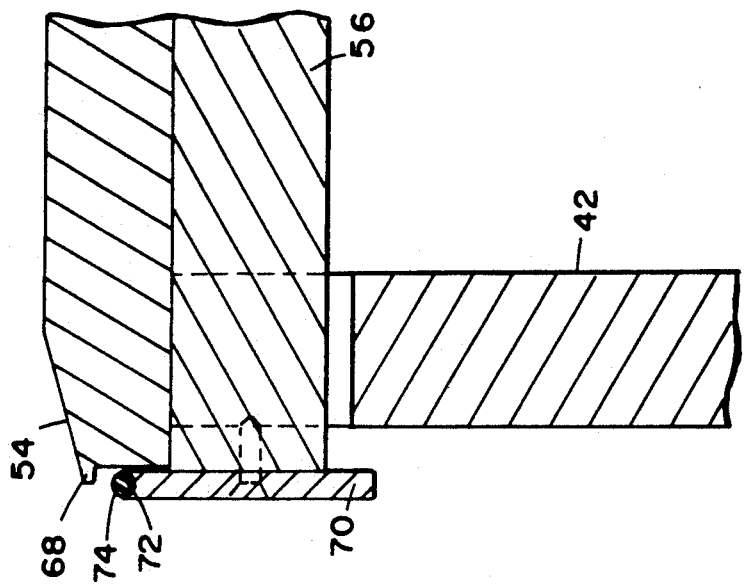
Figure 6:
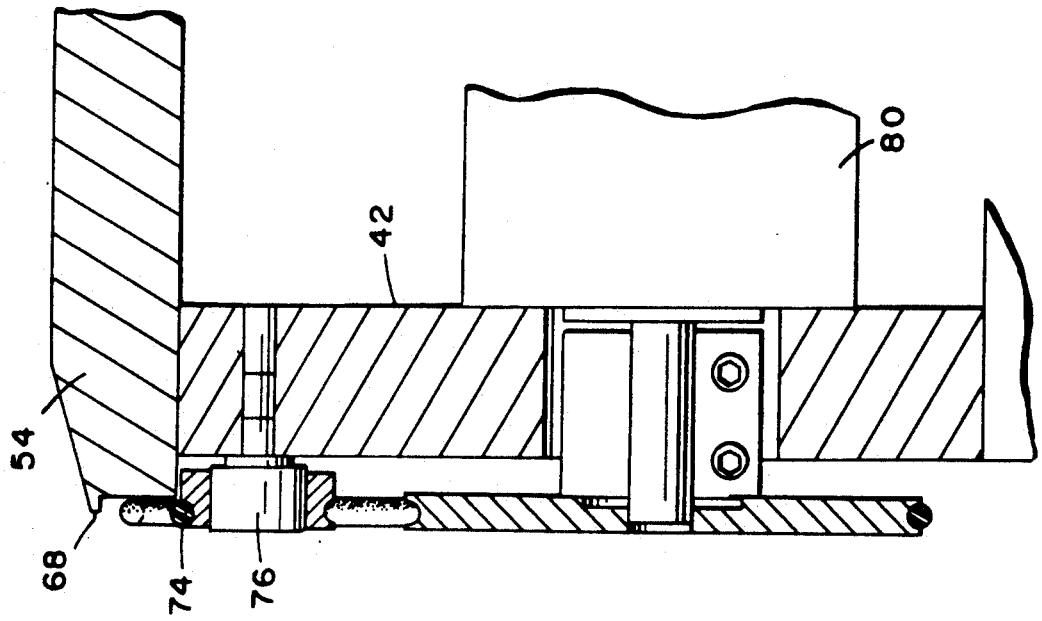
Figure 9:
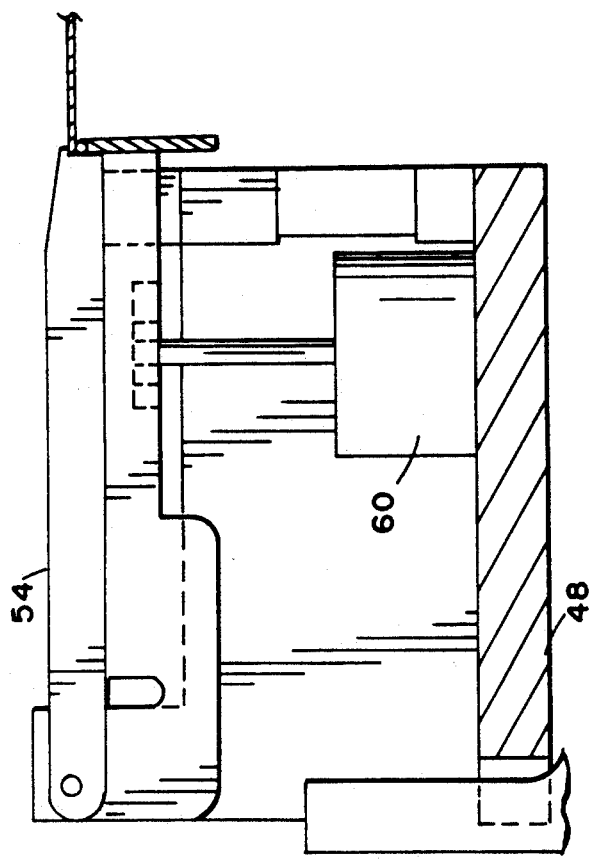
Figure 8:
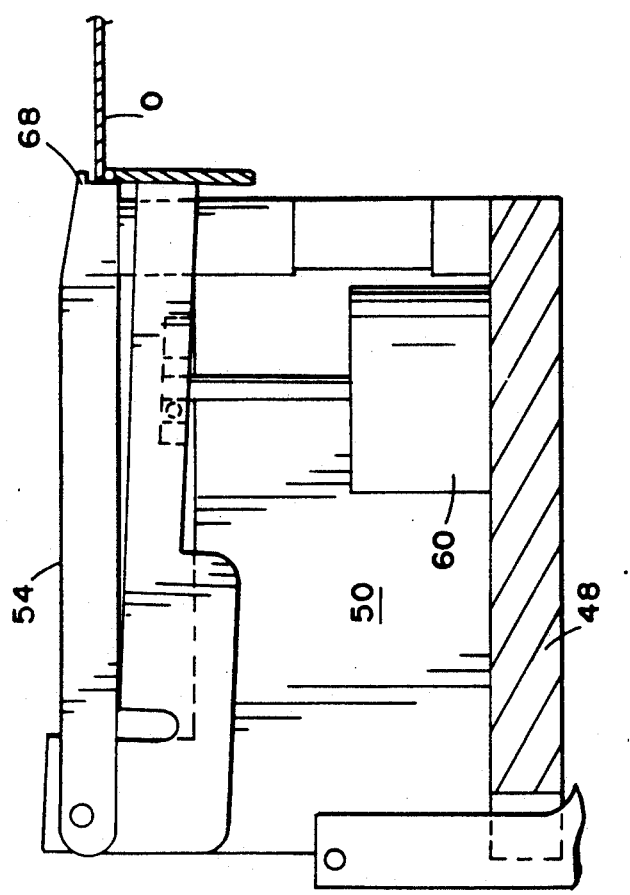
Figure 12:
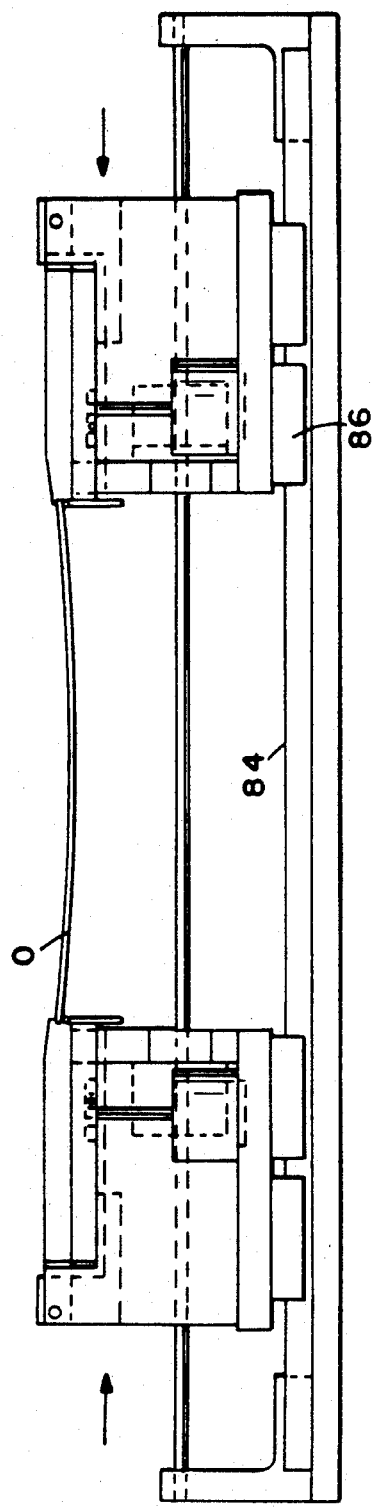
Figure 13:
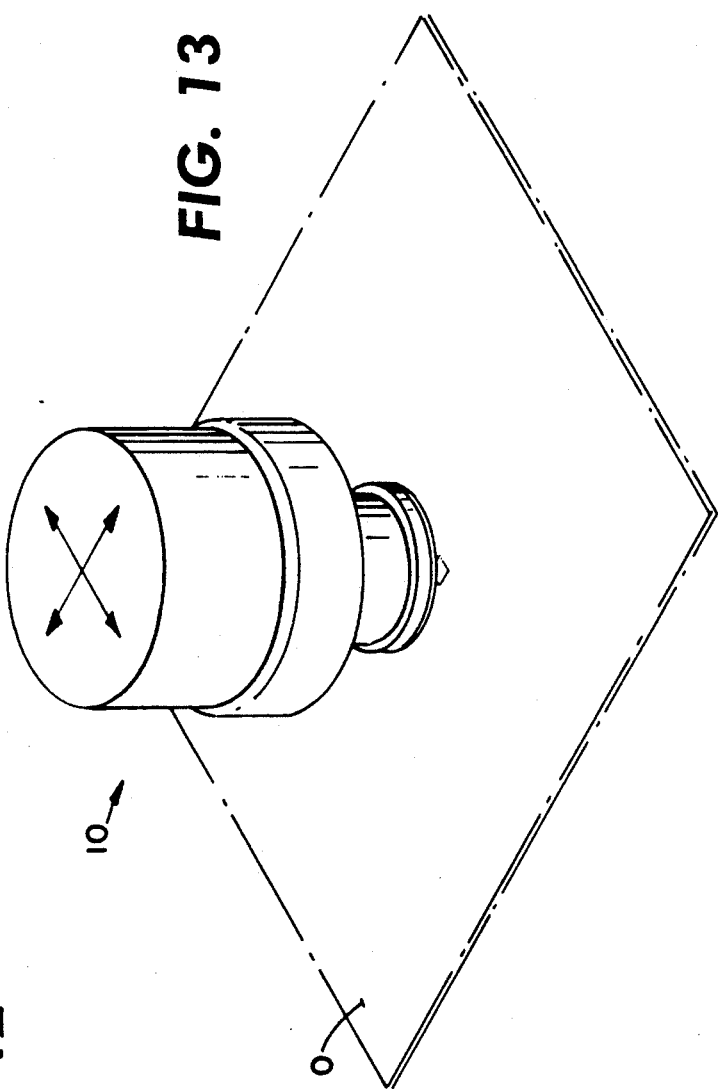

FIGS. 4 and 5 are cross-sectional views thereof taken generally about on lines 4—4 and 5—5 in FIG. 3;

FIGS. 6 and 7 are enlarged fragmentary cross-sectional views thereof taken generally about on lines 6—6 and 7—7 in FIG. 4;

FIGS. 8 and 9 are enlarged cross-sectional views of a representative side section of the conveyor illustrating the various positions of the clamping elements for clamping the margin of an object therebetween;

FIGS. 10 and 11 are end views illustrating the sag or bow of the board carried by the conveyors and also the manner of effecting planarity of a portion of the board and a plane normal to the axis of the lens;

FIG. 12 is an end elevational view illustrating the movement of the side sections toward and away from one another; and FIG. 13 is a schematic representation of the X-Y movement of the optical instrument relative to the board.

DETAILED DESCRIPTION OF THE DRAWING FIGURES

Reference will now be made in detail to a present preferred embodiment of the invention, an example of which is illustrated in the accompanying drawings.

Figure 1:
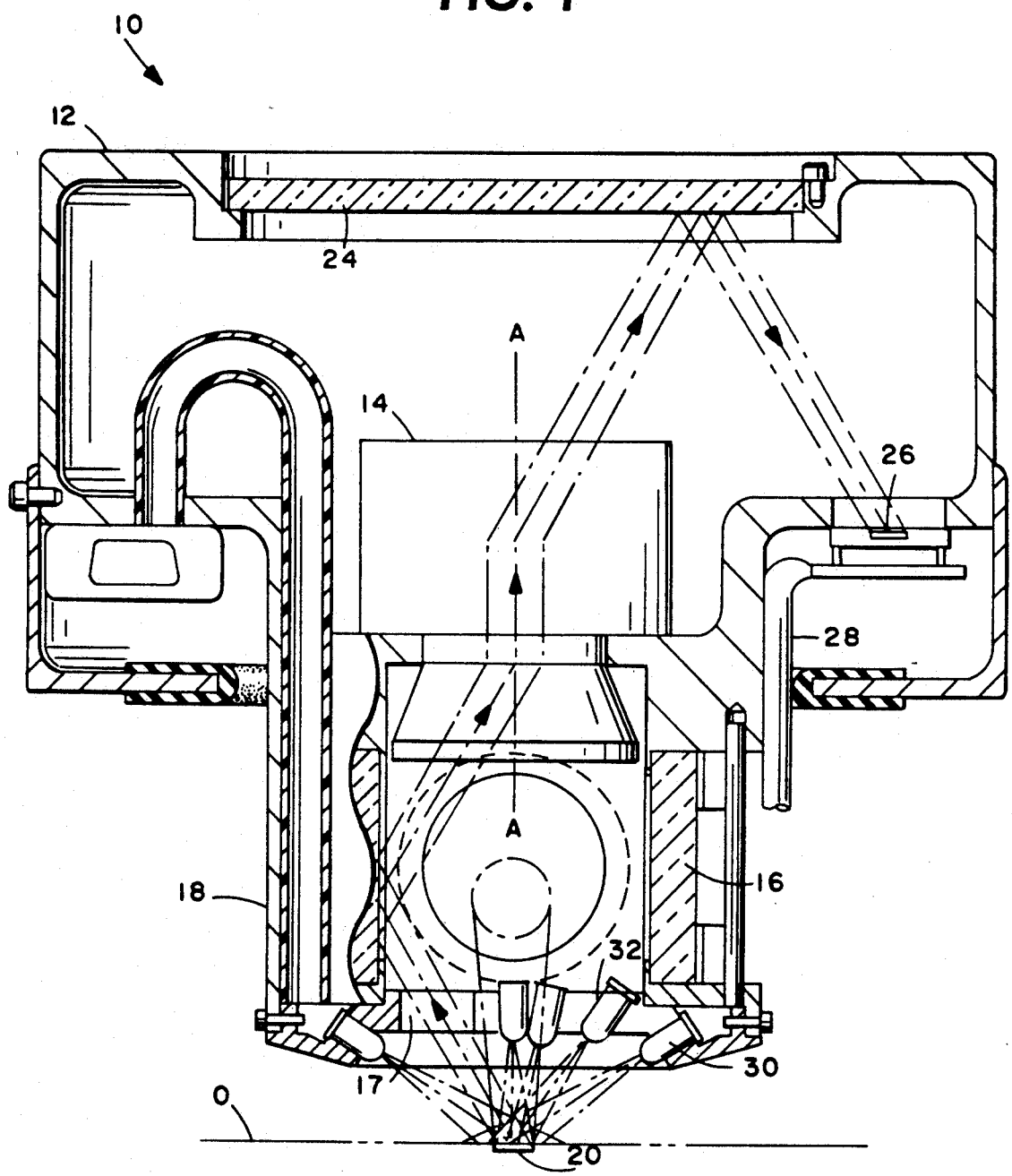
FIG. 1 is a cross-sectional view of an optical instrument constructed in accordance with the present invention.
Figure 2:
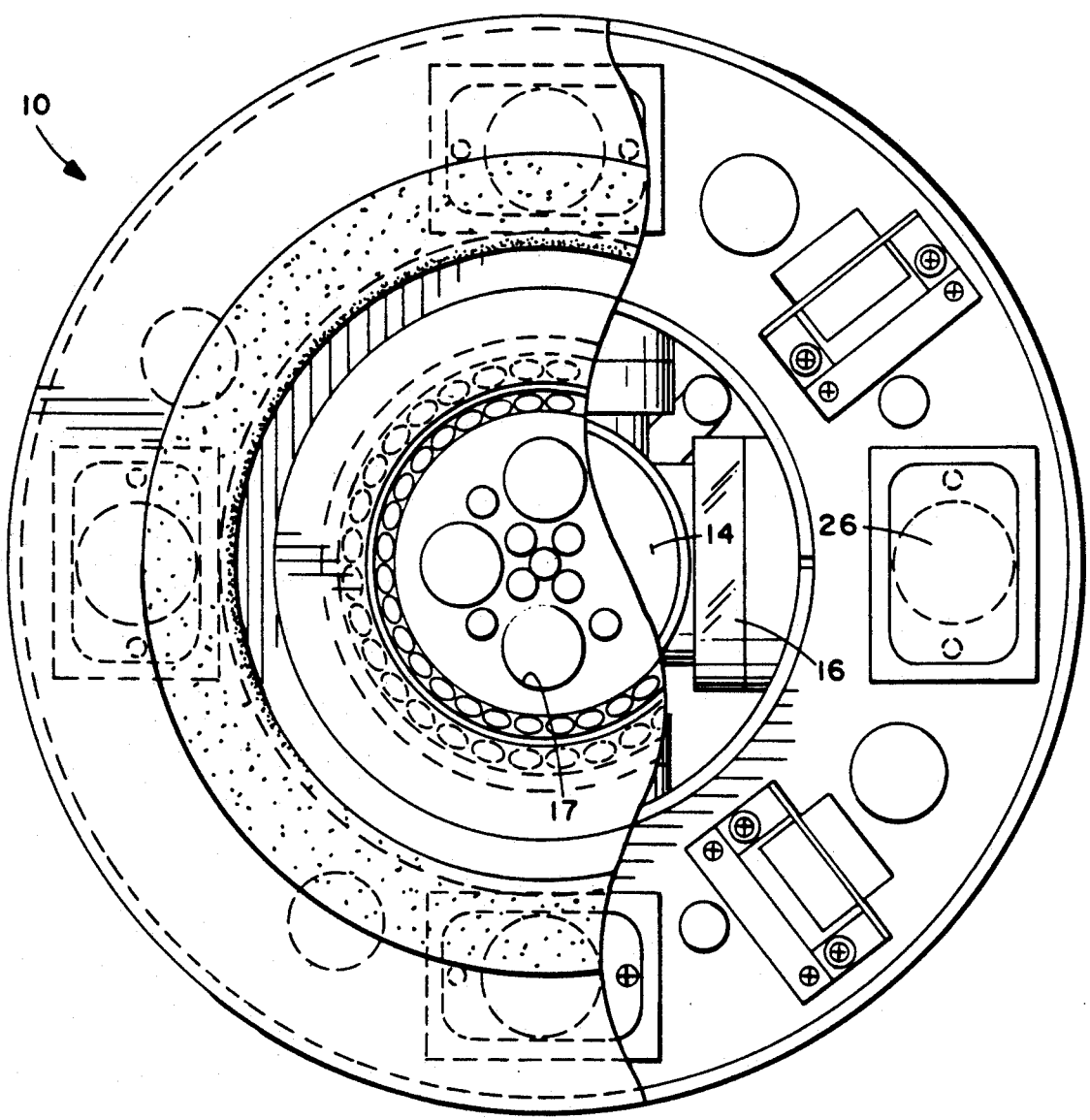
FIG. 2 is a plan view, with parts broken out for illustrative purposes, of the optical instrument of FIG. 1.

Referring now to the drawings, particularly to FIGS. 1 and 2, there is illustrated an optical instrument, generally designated 10, constructed in accordance with the present invention. Instrument 10 includes a body 12 mounted for movement in a plane, preferably an X-Y horizontally disposed coordinate system. The body 12 includes a wide-angle lens 14 having an axis A extending perpendicular or normal to an object 0 represented by the dashed lines below instrument 10. Body 12 includes a plurality of flat collecting mirrors 16 disposed about and spaced from the axis A of lens 14 and between the lens 14 and apertures 17 formed through the lower portion 18 of body 12. Collecting mirrors 16 are preferably symmetrically disposed about axis A with their flat mirrored sides parallel to axis A and located such that light rays from the object under observation, i.e., a portion 20 of the object under observation, pass through an associated aperture 17 for reflection from the flat surface collecting mirrors 16 at an angle through the wide-angle lens 14. While four collecting mirrors 16 are illustrated, it will be appreciated that any number of collecting mirrors may be used at some angle to Axis A.

To reduce the size of, and hence provide a compact vision head, a reversing mirror 24 is preferably disposed in the upper portion of body 12 for reflecting light rays passing through the wide angle lens 14 onto sensors 26. Sensors 26 are conventional in construction and convert the light rays into electrical signals which may be transmitted in analog form via wire guides 28 for digitization and analysis in a computer, not shown. The sensors 26 are disposed about the body 12 on opposite sides from its associated collecting mirror 16, respectively, wherein light rays are reflected from the object 20 through the wide angle lens 14 for reception on the sensors 26. Accordingly, the number of sensors 26 preferably corresponds to the number of collecting mirrors 16.

To achieve a compact vision head, a plurality of LEDs 30 for illuminating the object 20 are preferably disposed about the bottom of head 12 in a circular array. Additional LEDs 32 are disposed in other arrays about the apertures 17 for illuminating the object. Note that the LEDs are arranged to illuminate the exposed upper surface of the objects 20, as well as the angled surfaces along the sides of the object 20.

In using the optical instrument, it will be appreciated that the instrument is located in close proximity to the portion of the object intended for observation. With the portion 20 illuminated by the LEDs 30 and 32, the light rays from the object portion 20 pass at an angle, for example, an angle 30° to the axis A of lens 14, through apertures 17 for reflection by the collecting mirrors 16 through lens 14. The light rays emerging from lens 14 are reflected by reversing mirror 24 onto the sensors 26. It will be appreciated that the vertical or three-dimensional portions of the object portion 20 are clearly represented in the images impacting sensors 26. For example, light rays from the left edge of the object portion 20 are reflected by the collecting mirror 16, passed through wide-angle lens 14, reflected by reversing mirror 24 and appear along the right side of sensor 26. By the arrangement of the collecting mirrors and wide-angle lens, the image of the object is undistorted and of uniform focus for all three-dimensional surfaces of the object portion. Additionally, the brightness and magnification among the various images are identical.

Referring now to FIGS. 3-12, conveyor 40 includes a pair of side sections 42 on opposite sides of the direction of travel of conveyor 40 indicated in FIG. 3 by the arrow T. In FIG. 3, a circuit board is illustrated, by dashed lines, between side sections 42. In FIGS. 3-7, each side section 42 includes a fixed frame 44 to which is attached a base 45 mounting transversely extending rails 47. A transversely movable side plate 46 and bottom plate 48 are mounted on rails 47 by guides 49 carried along the undersurface of bottom plate 48. A pair of upright plates 50 are fixed to the bottom plate 48 and provide a common pivotal mounting about a dowel 52 for a pair of clamping elements 54 and 56. Clamping elements 54 and 56 comprise upper and lower clamping plates, each pivoted about dowels 52. The operating arms 58 of a pair of linear actuators 60 mounted on base plate 48 are pivotally secured to the lower clamping plate 56. Actuators 60 pivot lower clamping plate 56 relative to and into abutment with upper clamping plate 54 and, when engaged with one another, both clamping plates jointly pivot about dowels 52.

As best illustrated in FIG. 7, clamping plate 54 has a projecting lip 68, while the lower clamping plate 56 includes an elongated plate 70 having an upper groove 72 for receiving the belt 74 of an endless conveyor belt loop. Belt 74 is disposed about idler pulleys 76 at opposite ends of frame 46 and about a pair of idler pulleys 78 which straddle a conveyor motor 80. Motor 80 drives belt 74 to convey an object disposed between the side sections in the direction of the arrow T illustrated in FIG. 3. As illustrated in FIG. 7, belt 74 on plate 70 is spaced just below lip 68 to accommodate the margin of the object, e.g., a circuit board, to be conveyed. It will be appreciated that plate 70 is mounted for pivotal movement with lower plate 56 whereby the belt 74 in groove 72 can be spaced from lip 68 to accommodate the margin and then displaced toward lip 68 to clamp the margin of the object. A horizontal linear actuator 82 is disposed between the side frame 46 and a frame member 87 fixed to fixed frame 44 whereby the side sections can be moved toward and away from one another in response to actuation of the linear motor.

When a board or object is disposed between the side sections, the belt 74, as illustrated in FIGS. 8 and 9, serves as a support for the margin of the board, with the lower clamping plate 56 in a lowered position. Upon actuation of the vertical linear actuator 60, plate 70 is displaced toward lip 68 to clamp the margin of the board, as illustrated in FIG. 9, between belt 74 and lip 68 whereby the board may be stopped along the conveyor. As illustrated in FIG. 12, the side sections of the conveyor may be displaced along the guide rails 47. Also as seen in FIG. 12, the object O in this illustration comprising a circuit board bows or sags downwardly.

In using the device and with reference to FIGS. 10, 11 and 12, it will be seen that the vision head is disposed above the board and is spaced a predetermined distance S according to the focal length of the wide-angle lens from the conveyance plane of the board, e.g., its horizontal plane of conveyance. It will be appreciated that any sag or bow in the board will cause the small portion of the board under observation, as illustrated by the dashed line in FIG. 13 and under the dashed line configuration of the optical instrument in FIG. 10, to lie in a plane which is non-parallel to a plane perpendicular to the axis A of the lens. That is, where the board is conveyed in a horizontal plane, the sagging portion forms an angle with the horizontal and at least portions of the board are incorrectly spaced from the head. Because of the tilt or non-parallel relation of the object portion relative to the horizontal, and its incorrect spacing, the image will be distorted and displaced differently at each image sensor. To correct this image distortion and incorrect displacement in accordance with the present invention, the clamping elements along the opposite sides of the conveyor are displaced relative to one another in accordance with the transverse location of the optical instrument relative to the board. For example, as illustrated in FIG. 10, the object portion below the dashed line showing of the optical instrument tilts from left to right in a downward direction. To correct that tilt and reorient the tilted object portion back into the plane of conveyance, e.g., a horizontal plane, the opposite margin of the circuit board is elevated to raise the board and locate the object portion in a plane substantially parallel to the conveyance plane, e.g., the horizontal plane, and immediately below the vision head. This is accomplished by actuating the vertical actuators 60 to pivot the clamping elements as illustrated in FIG. 11 in the direction of the arrow.

As illustrated in FIG. 13, the optical instrument is mounted on an X-Y coordinate system for movement transversely and longitudinally relative to the circuit boards such that object areas of interest on the board may be observed. Upon shifting the instrument along the X-Y coordinates, and knowing its location along those coordinates, the clamping elements of the side sections of the conveyor can be displaced relative to one another to locate the object portion being observed in a plane generally parallel to the conveyance plane, e.g., the horizontal plane, as previously described. For example, the right side conveyor section as illustrated in FIG. 11 has its clamping elements pivoted relative to the left side clamping elements to bring the object portion located along the left side of the board into a plane generally parallel to a horizontal plane. When the optical instrument lies on the right side of the board, the reverse operation occurs. When the optical instrument is located medially between the opposite sides of the conveyor sections (as illustrated by the full line showing of head 10 in FIG. 10), both clamping elements on each side of the conveyor section are elevated to raise the object into the proper distance S from the lens for proper focussing and into the proper plane.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An optical device for providing discrete, undistorted and uniform images of an object lying in a plane and having three-dimensional surfaces, with each image taken at a different angular location about an axis passing perpendicularly through the plane and object, comprising:

a wide angle lens spaced from the object and disposed along the axis;

a plurality of collecting mirrors spaced from and disposed at predetermined angular locations about said axis, said mirrors lying in planes generally parallel to said axis and for disposition between said wide angle lens and the object for reflecting light rays from the object through said wide angle lens; and means for receiving the light rays passing through said wide angle lens from the object and said collecting mirrors representing an undistorted image of the object as viewed from each angular location with uniform focus of the three dimensional surfaces of the object.

2. A device according to claim 1 wherein said lens and said collecting mirrors are mounted on a frame, and means carried by said frame for illuminating the object.

3. A device according to claim 1 including reversing mirror means for shifting the focus of the light rays through said lens onto said receiving means.

4. A device according to claim 3 wherein said receiving means are spaced one from the other about said axis and outwardly of said wide angle lens, said reversing mirror means being disposed above said wide angle lens, said receiving means including sensors for converting light images into electrical signals.

5. A device according to claim 4 wherein said lens and said collecting mirrors are mounted on a frame, and means carried by said frame for illuminating the object.

6. A visual inspection machine for visually inspecting surface portions of generally planar extending elements comprising:

a conveyor for conveying the elements with each element having surface portions in a first plane and displacing such surface portions into a second, different plane;

said conveyor including first and second conveying sections spaced one from the other with each section including means for engaging a marginal portion of the element spanning between said sections for conveying the element in a predetermined direction of conveyance;

means carried by each said first and second conveyor sections for displacing the respective margins of the element in a direction generally normal to the direction of conveyance and independently of one another whereby a specified surface portion of the element in said first plane may be disposed in said second plane;

an optical device for providing discrete undistorted images of the surface portion of said element when lying in said second plane and disposed in spaced registration with an element on said conveyor;

a wide angle lens spaced from the surface portion of the element and having an axis generally normal to said second plane;

a plurality of collecting mirrors spaced from and disposed at predetermined angular locations about said axis, said mirrors lying in planes generally parallel to said axis and for disposition between said wide angle lens and the element for reflecting light rays from the element through said wide angle lens; and means for receiving the light rays passing through said wide angle lens from the element and said collecting mirrors representing an undistorted image of the element as viewed from each angular location with uniform focus of the three dimensional surfaces of the element.

7. A visual inspection machine according to claim 6 wherein said lens and said collecting mirrors are mounted on a frame, and means carried by said frame for illuminating the element.

8. A device according to claim 6 including reversing mirror means for shifting the focus of the light rays through said lens onto said receiving means.

9. A device according to claim 8 wherein said receiving means are spaced one from the other about said axis and outwardly of said wide angle lens, said reversing mirror means being disposed above said wide angle lens, said receiving means including sensors for converting light images into electrical signals.

10. A method of optically inspecting an object, comprising the steps of:

conveying an object in a first predetermined direction with a surface portion of the object in a first plane;

displacing a margin of the object in a direction generally normal to the direction of conveyance and independently relative to an opposite margin of the object to reorient the surface portion from said first plane into a second plane different from said first plane;

providing a wide angle lens having an axis generally normal to the surface portion in said second plane and a plurality of collecting mirrors about said axis and between said lens and the surface portion; and optically forming images of the surface portion of the object in the second plane from different angular locations about said axis with each image representing an undistorted image of the surface portion as viewed from each angular location with uniform focus of the three-dimensional surfaces of the object.

11. A method according to claim 10 including the step of displacing at least one margin of the object in a direction generally normal to the direction of conveyance to locate the surface portion a predetermined distance from said lens.

12. A method according to claim 10 including the step of displacing said wide angle lens in X-Y directions in a plane spaced from and parallel to said second plane to optically inspect a plurality of surface portions in the object.

13. A method according to claim 10 including providing conveyor sections along opposite sides of the conveyor and displacing at least one conveyor section toward the other conveyor section for conveying objects of different widths.

* * * * *